United States Patent [19]

Täger

[11] Patent Number: 5,147,407
[45] Date of Patent: Sep. 15, 1992

[54] PROSTHETIC CUP MEMBER

[76] Inventor: Karl H. Täger, Fichtenstrasse 1, D-8035 Gauting, Fed. Rep. of Germany

[21] Appl. No.: 776,122

[22] Filed: Oct. 15, 1991

[30] Foreign Application Priority Data

Oct. 20, 1990 [DE] Fed. Rep. of Germany ....... 9014542

[51] Int. Cl.[5] .............................................. A61F 2/34
[52] U.S. Cl. ..................................................... 623/22
[58] Field of Search ....................... 623/22, 16, 18, 20, 623/23

[56] References Cited

U.S. PATENT DOCUMENTS

| Re. 31,865 | 4/1985 | Roux | 623/22 |
|---|---|---|---|
| 3,894,297 | 7/1975 | Mittelmeier et al. | 623/22 |
| 4,662,891 | 5/1987 | Noiles | 623/22 |
| 4,715,859 | 12/1987 | Schelhas et al. | 623/22 |
| 4,795,469 | 1/1989 | Oh | 623/22 |
| 4,795,470 | 1/1989 | Gaymann et al. | 623/22 |
| 4,813,961 | 3/1989 | Sostegni | 623/22 |
| 4,822,367 | 4/1989 | Stuhmer | 623/22 |
| 4,834,759 | 5/1989 | Spotorno et al. | 623/22 |
| 4,871,368 | 10/1989 | Wagner | 623/22 |
| 4,878,916 | 11/1989 | Rhenter et al. | 623/22 |
| 4,883,491 | 11/1989 | Mallory et al. | 623/22 |
| 4,894,064 | 1/1990 | Imhof | 623/22 |
| 4,919,676 | 4/1990 | Zweymuller et al. | 623/22 |
| 4,963,154 | 10/1990 | Anapliotis et al. | 623/22 |

FOREIGN PATENT DOCUMENTS

| 0179736 | 4/1986 | European Pat. Off. | 623/22 |
|---|---|---|---|
| 0303006 | 5/1988 | European Pat. Off. | |
| 0329019 | 2/1989 | European Pat. Off. | |
| 2301810 | 7/1973 | Fed. Rep. of Germany | 623/22 |
| 2622432 | 5/1989 | France | 623/22 |
| 2630907 | 11/1989 | France | 623/22 |
| 2154141 | 9/1985 | United Kingdom | 623/22 |

*Primary Examiner*—David Isabella
*Attorney, Agent, or Firm*—Peter C. Richardson; Lawrence C. Akers; Raymond W. Augustin

[57] ABSTRACT

A prosthetic cup member, in particular for use in the hip joint, has a hollow outer shell which is adapted to be affixed to the bone. The cup has an inner shell having a recess for accommodating a bearing element. The inner shell and the outer shell are spaced radially from each other at a predetermined distance to define an intermediate space therebetween. The outer surface of the outer shell has coaxial threads interrupted by grooves extending transversely to the thread. The threads are self-tapping threads and are formed to permit the threaded outer shell to be screwed into the bone. The outer shell has a plurality of elongated openings or slots connected to the intermediate space to permit loose spongious material such as cancellous bone, to be introduced into and held in the intermediate space during surgical emplacement of the cup member. This enhances the growth of new bone tissue into the intermediate space. The elongated openings extend over almost the entire axial length of the outer shell.

13 Claims, 3 Drawing Sheets

PROSTHETIC CUP MEMBER

BACKGROUND OF THE INVENTION

1. Field of the Invention

The invention relates to a prosthetic joint socket member, in particular for a hip prosthesis. More particularly, this invention relates to an acetabular cup.

2. Description of the Prior Art

Prostheses for the replacement of hip joints have been used for many years. these prostheses usually includes s stem portion on which a spherical ball is mounted and an acetabular portion or socket member for implantation is in the natural acetabulum. Alter naively, the acetabular prosthetic cup may receive the ball of the natural femur which may be may not be resurfaced.

From German patent specification 23 01 801, it is known to make a cup member from a hollow outer shell and an inner shell. The inner shell has a recess for accommodating the ball. Due to the forces acting on the cup member, the cup member may become loosened in the bone. European patent specification 0 303 006 discloses a method to provide the outer surface of the cup member with small balls in order to improve the in growth of the prostheses int h bone material.

european patent specification 0 329 019 discloses a cup member consisting of an outer an an inner shell to be screwed into the hip bone. The outer hollow shell has circular or elongated openings permitting spongiosa or loose bone substance to be introduced into and securely held in the intermediate space between outer and inner shell. The introduction of this material can be carried out during the operation and thereafter ensures growth there into of a new wrong bone substance. The outer surface of the outer shell has thread portions interrupted by grooves which form a tapping thread.

The affixing of the joint socket member is predominantly affected by screwing the socket body portion into the bone substance by means of the self-tapping screw thread, and the anchoring of the prosthesis is increased by the in growth of bone material.

SUMMARY OF THE INVENTION

It is an object of the invention to provide an acetabular cup ro socket member which can be more effectively screwed into The bone.

It is another object of the invention to provide an acetabular cup or socket member which has improved bone ingrowth characteristics.

The acetabular cup or socket member according to the present invention has an inner and outer shell defining an intermediate space with longated openings fromed in the outer shell extending approximately the axial length thereof, which openings additionally form grooves for the self-tapping screw thread. The orientation of the openings transverse to the circumferentially and coaxially extending thread portions not only allows a simple insertion of spongiosa or the like into the intermediate space, but in addition, allows the one chips generated during the placement of the cup member to enter the intermediate space. The bone material in the intermediate space is prevented from escaping during the operation.

In the cup of the present invention, thee longated openings or slots have an optimum extension of approximately the total axial length of the cup member so that growth of bone material into the cup member can take place about a large surface area. This bone ingrowth anchors the cup member safely and permanently within the acetabulum.

According to a preferred embodiment of the invention, the self-taping screw thread is double-treaded whereby an additional positive retaining force is achieved. According to a second embodiment of the invention, the elongated openings are milled in the outer shell at an angle to the axis of the shell, preferably at an angle of about 30°. The openings are also milled at an angle to the radius of the shell, i.e. The axis of the feed during milling is inclined towards the rotational direction, preferably at an angle of 10°.

The height and length of the thread portions increase towards the distal end of the cup element and, thus, decease the screw-in torque. This embodiment, in combination with the elongated slots and the double threaded of the tapping screw thread, facilitates the insertion of a cup element and improves its anchoring after emplacement.

The outer and inner shell can be integrally cast. Alternatively, both shells can be cast separately. Thereafter, the inner shell is fitted into the outer shell, and both shell parts can be interconnect, for example, by cold welding.

According to a preferred embodiment of the invention, the inner and outer shells are conical, with the inner shell having a groove to be ingaged by a tool to screw the cup member into the hip bone. A correspondingly formed insert may be inserted into the inner shell, having projections cooperating with the mentioned groove of the inner shell, thus affecting a locking of the insert in the inner shell. The preferred insert for the cup member has an annular radial flange which is engaged by a radial flange of the inner shell, with the outer shell engaging the flange to the inner shell.

These and other objects and advantages to the present invention will become apparent from the following description the accompanying drawings, which disclose one embodiment to the invention. It is to be understood that the drawings are to be used for purposes of illustration only, and not as a definition of the invention.

BRIEF DESCRIPTION OF THE DRAWINGS

In the drawings, wherein similar reference characters denote similar elements throughout the views.

DESCRIPTION OF THE PREFERRED EMBODIMENT

Referring to FIGS. 1 through 7, the cup member, generally denoted as 1, consists of an outer shell 10 facing the hip bone (not shown) after emplacement therein and an inner shell 20 into which an insert 40, such as a standard polyethylene inset, is inserted.

Figure 1:
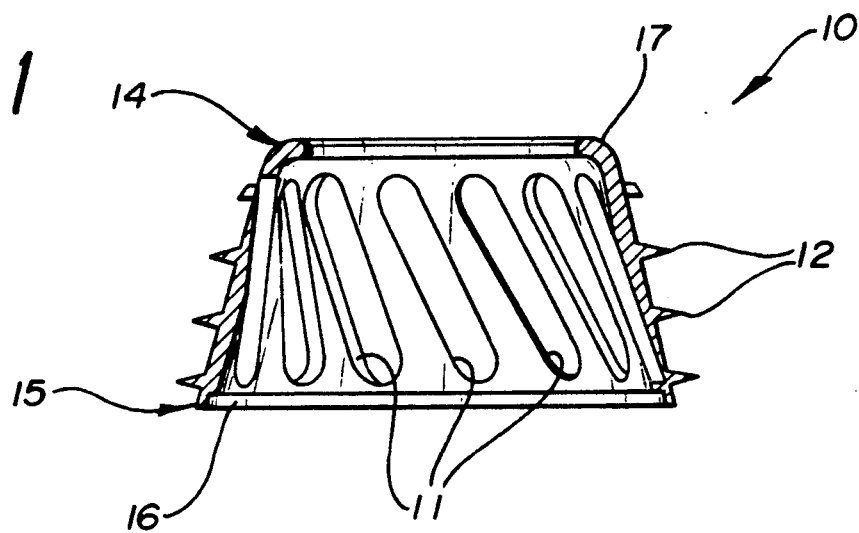
FIG. 1 is a cross-sectional view of through the outer shell of the cup member of the present invention.
Figure 2:
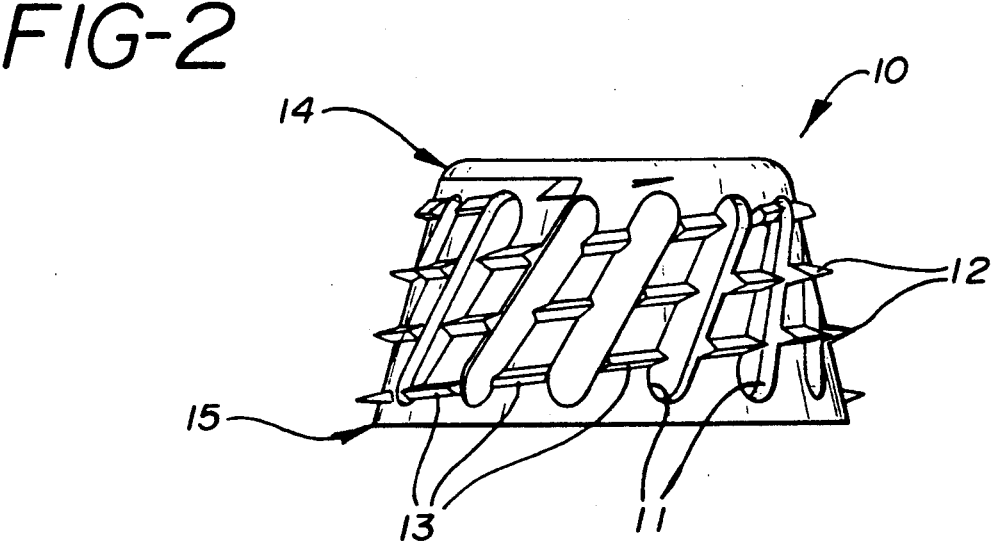
FIG. 2 is a side view of the outer shell shown in FIG. 1.
Figure 3:
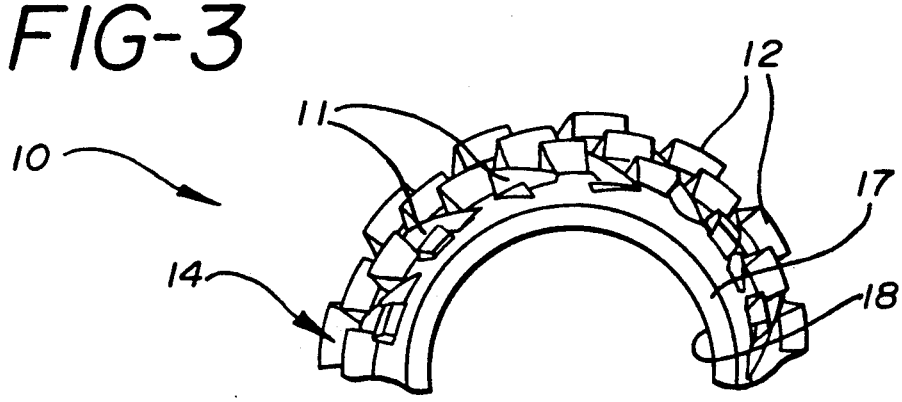
FIG. 3 is a partial plan view of the outer shell of FIG. 1.

Outer shell 10 of cup element 1 preferably has a conical shape and has a plurality of circumferentially spaced elongates lots or openings 11 extending at an angle to the axis of outer shell 10 over a majority of the total axial length thereof. As can be seen in FIG. 1, openings 11 are milled at angle of 30° with respect to the axis and at an angle of 10° with respect to the radius, i.e. The walls of the openings are inclined towards the rotational direction of outer shell 10. The outer side of outer shell 10 has a plurality of discrete thread portions 12. As can be seen in FIG. 2, the thread portions 12 form a plurality of rows 13 extending at an angle to the axis of outer shell 10 between openings 101. As can be seen in FIG. 3, the height and the length of the thread portions decrease towards the proximal end 14 of outer shell 10. The elongated openings 11 between rows 13 of thread portions 12 act in the same way as a groove formed on a tapping tool. A circumferential groove 16 is formed at the inner side at the distal end 15 of outer shell 10. At the proximal end 14, outer shell 10 is radiused at 17 and exposes an opening 18.

Figure 4:
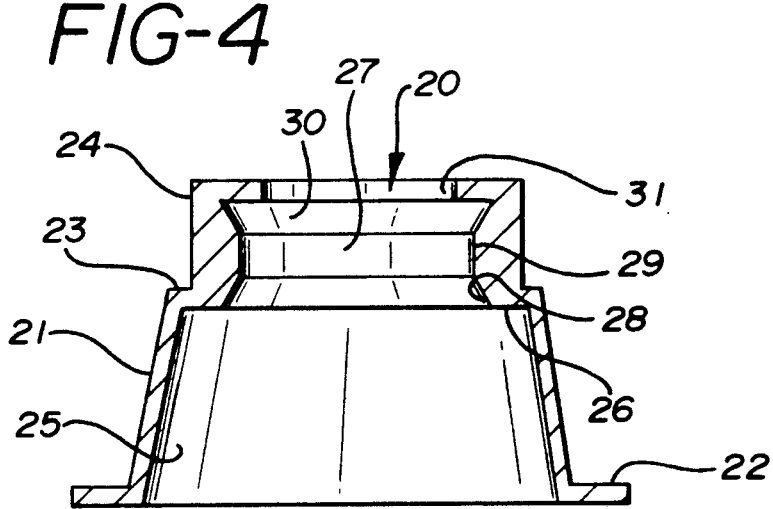
FIG. 4 is a cross-sectional view through the inner shell of a cup of the invention.

Referring to FIG. 4, inner shell 20 of cup element 1 has a conical portion 21 including a radial flange 22 and a cylindrical portion 24 joined to conical portion 21 through a shoulder 23. Conical portion 21 forms a conical space 25 terminating at a shoulder 26. A conical portion 28 joins to the conical space 25 and in turn is joined to a cylindrical portion 29. /a groove 30 is formed adjacent to the cylindrical portion 29. At the proximal end the inner shell has an opening 20' defined by a circular edge 31.

Figure 5:
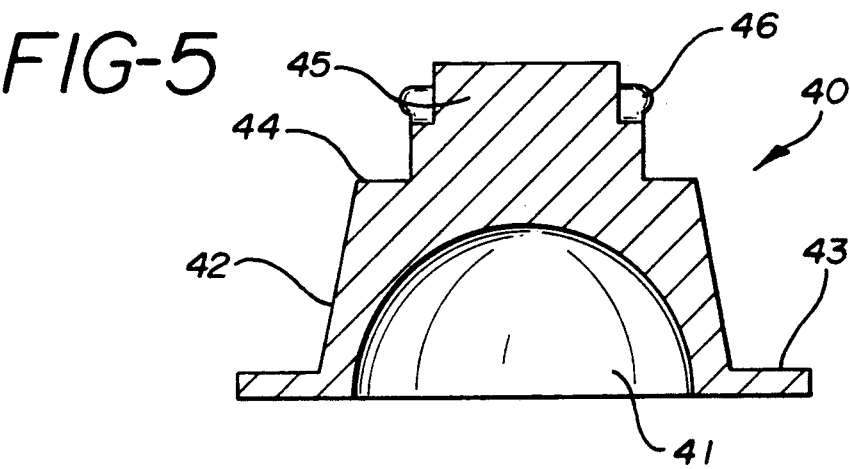
FIG. 5 is a cross-sectional view through an insert for the cup of the invention.
Figure 6:
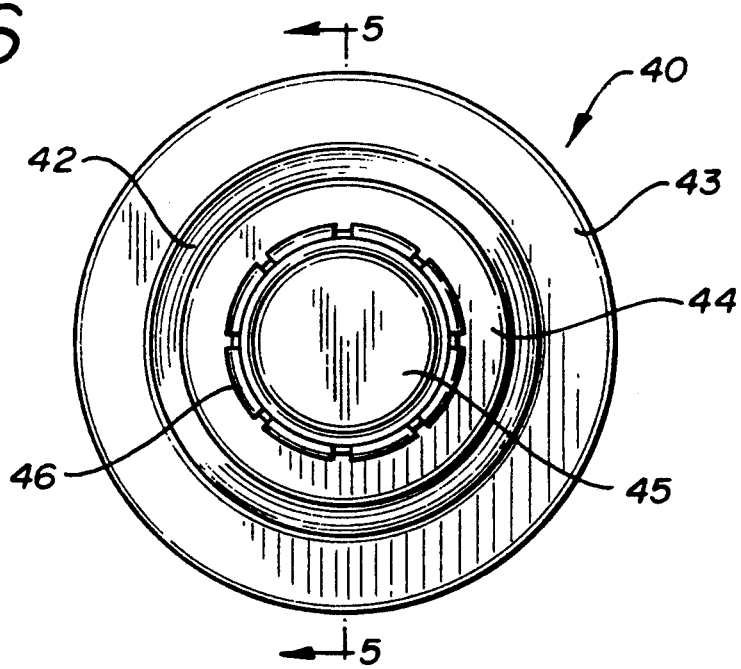
FIG. 6 is a plan view to the insert of FIG. 5.

Referring to FIG. 5, there is shown a insert 40 which has a hemispherical recess 341 for the accommodation to a joint ball. Recess 41 is formed on the inner surface of a conical portion 42. A axial flange 43 is formed at the distal end of conical portion 42; The opposite end of portion 42 includes a shoulder 44, and a portion 45 extending proximally from shoulder 44, with six projections 46 being integrally formed at the outer side of portion 45 as can be seen in FIG. 6.

Figure 7:
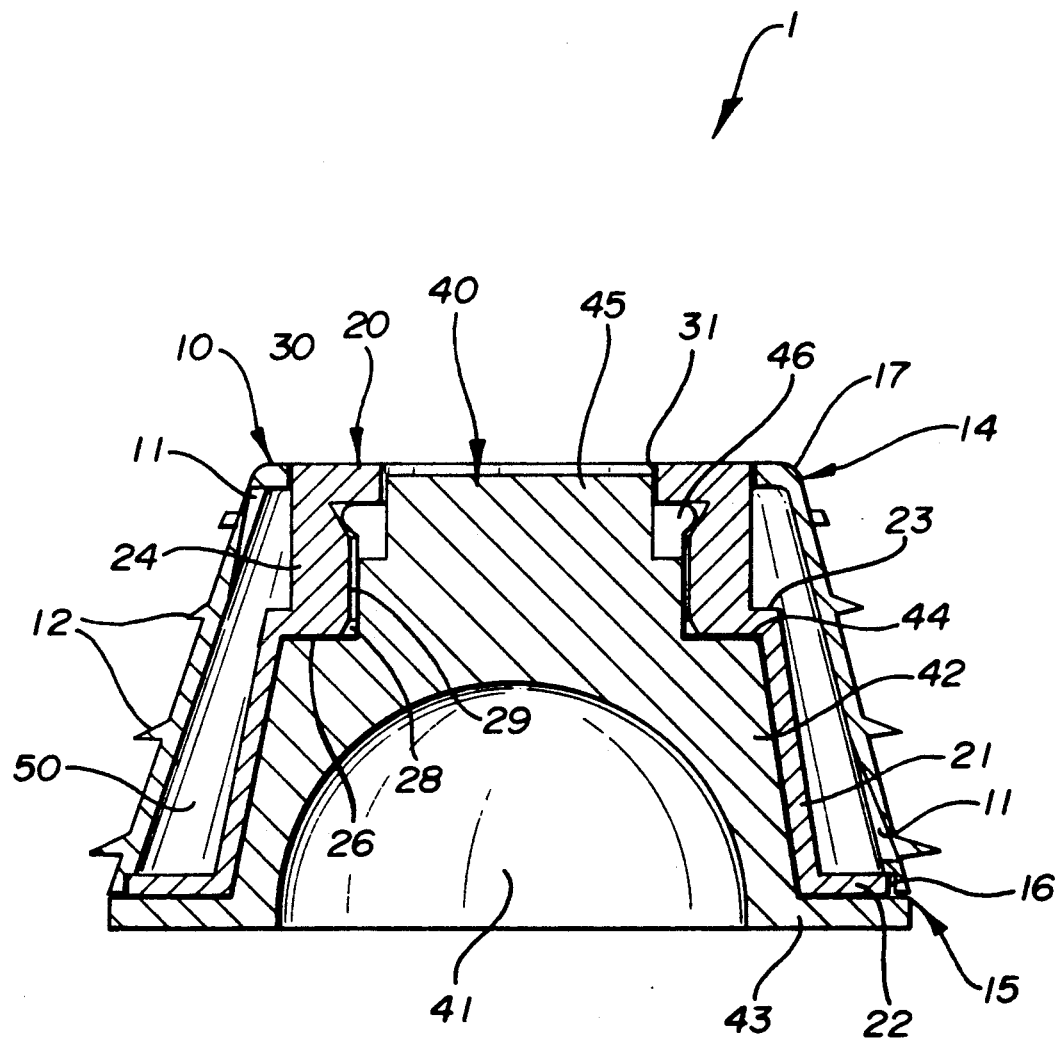
FIG. 7 is a cross-section through a cup including the outer shell, inner shell and the insert.

Referring to FIG. 7, there is shown the assembly of inner shell 20 and outer shell 10. Flange 22 of inner shell is accommodated by groove 16 of outer shell 10, while cylindrical portion 24 is fittingly accommodated by opening 18 of outer shell 10. An annulars conical intermediate opening space 50 is defined between outer shell 10 and inner shell 20 into which, before emplacement of cup element 1, loose bone material can be inserted through elongated openings 11. The self-tapping thread portions 12 allow cup element 1 to be effectively screwed into the hip bone acetabulum by means of a tool (not shown).

Upon insertion of insert 40 into inner shell 20, the projections 46 are temporarily deformed by the cylindrical portion 29 of inner shell 20 until they engage groove 30 so that insert 40 is locked within the inner shell. Shoulder 44 of insert 40 engages shoulder 26 of inner shell 20 and the lower side of radial flange 22 of the inner shell engages the radial flange 43 of insert 40.

The cylindrical portion 4 of insert 40 is within the cylindrical portion 27 of inner shell 20 and is angularly encircled by cylindrical portion of inner shell 20 which fittingly engages opening 18 of outer shell 10 so that opening 18 sis substantially closed by the proximal end surfaces of insert 40 and inner shell 20 approximately at the level of the proximal outer side of outer shell 10.

After implantation of cup or socket member 1, bone material can grow into the intermediate space 50 through the elongated openings 11 and interconnect with the bone substance within the intermediate space in order to safely anchor the cup member in the hip bone.

The inner and outer shell may be made separately and interconnected during fabrication such as by hot or cold welding.

While the cup member described above has been described for use as a prosthetic acetabular cup, such a cup could also be used in the replacement of a shoulder joint.

While several examples of the present invention has been described, it is obvious that many changes and modifications may be made there unto, without departing from the spirit and scope of the invention.

I claim:

1. A prosthetic cup member comprising:
   a hollow outer shell having an outer surface adapted to be affixed to the bone;
   an inner shell located within said outer shell and forming a recess for accommodating a bearing insert element, said inner shell and said outer shell being spaced radially from on another to define an intermediate space therebetween;
   the outer surface of said outer shell having coaxial than portions along an axial length thereof interrupted by grooves formed in the outer shell and bending transversely to said thread, said threads being self-tapping to permit said outer shell to be screwed into said bone, said grooves in said outer shell being in the form of elongated openings in said outer shell opening to said intermediate space to permit material to be introduced into and held within said intermediate space during surgical emplacement to the cup member so as to enhance the growth of new bone tissue into said intermediate space, said grooves formed by said elongated openings extending over the majority of the axial length of said outer shell.

2. The cup member as set forth in claim 1 wherein said self-tapping thread is a double thread.

3. The cup member as set forth in claim 1 wherein said elongated openings are located t an angle of about 30° to the axis of said outer shell.

4. The cup member as set forth in claim 1, wherein said outer shell has a surface formed as a section of a cone and said elongated openings are milled at an angle cross said conical surface of said outer shell at an angle of about 10° inclined to the rotational direction.

5. The cup member as set forth in claim 1, wherein the height of said thread portions increases from the proximal to the distal end of said outer shell.

6. The cup member as set forth in claim 1, wherein the length of said thread portions increases from the proximal to the distal end of said outer shell.

7. The cup member as set forth in claim 1, wherein the inner and outer shells of said cup element are integral cast.

8. The cup member as set forth in claim 1, wherein said outer shell nd said inner shell are made separately, with said inner shell being dimensioned to fit within said outer shell to form said intermediate space therebetween and includes means for interconnecting said inner shell to said outer shell.

9. The cup member as set forth in claim 1, wherein said outer shell and said inner shell have a generally conical form.

10. The cup member as set forth in claim 9, wherein said inner shell has a conical potion having a radial flange and a cylindrical portion engaging an opening formed at the proximal end of said ore shell and said radial flange engaging a circumferentially extending groove at the digital end of said outer shell.

11. The cup member as set forth in claim 10, wherein said groove is freed on an inner surface of said distal end of said outer shell and aid groove including means for accommodating a tool of threading said cup element into said hip bone.

12. The cup member as set forth in claim 10, further including a bearing inset element having a conical portion with a radial flange and a cylindrical portion, with said radial flange of said insert engaging the lower side of said radial flange of said inner shell.

13. The cup member as set forth in claim 12, wherein a plurality of circumferentially spaced projections are formed on said cylindrical portion of said insert, said projections engaging said groove of the cylindrical portion of said inner shell in order to lock said insert within said inner shell.

* * * * *